(12) United States Patent
Godo et al.

(10) Patent No.: US 6,432,069 B1
(45) Date of Patent: Aug. 13, 2002

(54) COUPLING MEDIUM FOR HIGH-POWER ULTRASOUND

(75) Inventors: Joseph Godo, Meaux; Emmanuel Blanc, St. Genis Laval, both of (FR)

(73) Assignee: Technomed Medical Systems, S.A., Vaulx-en-Velin (FR)

( * ) Notice: Subject to any disclaimer, the term of this patent is extended or adjusted under 35 U.S.C. 154(b) by 0 days.

(21) Appl. No.: 09/531,610

(22) Filed: Mar. 21, 2000

(30) Foreign Application Priority Data

Mar. 25, 1999 (FR) .............................. 99 03738

(51) Int. Cl.$^7$ .............................. A61H 1/00; A61H 1/02; A61H 5/00
(52) U.S. Cl. .............................. 601/2; 604/14; 604/22; 600/439
(58) Field of Search .............................. 601/2; 600/407, 600/437, 439, 458; 604/19, 22; 424/9.5

(56) References Cited

U.S. PATENT DOCUMENTS

| | | | |
|---|---|---|---|
| 4,886,068 A | 12/1989 | Kaneko et al. | 128/660.01 |
| 5,078,149 A | 1/1992 | Katsumata et al. | 128/662.03 |
| 5,323,769 A * | 6/1994 | Bommannan et al. | 601/2 |
| 5,445,813 A | 8/1995 | Schneider et al. | 424/9.51 |
| 5,558,092 A * | 9/1996 | Unger et al. | 128/660.03 |
| 5,666,954 A | 9/1997 | Chapelon et al. | 128/660.03 |
| 5,720,286 A | 2/1998 | Chapelon et al. | 128/660.03 |
| 5,720,287 A | 2/1998 | Chapelon et al. | 128/660.03 |
| 5,762,066 A * | 6/1998 | Law et al. | 128/660.03 |
| 6,071,238 A | 6/2000 | Chapelon et al. | 600/439 |
| 6,190,315 B1 * | 2/2001 | Kost et al. | 600/309 |
| 6,267,734 B1 * | 7/2001 | Ishibashi et al. | 601/2 |

FOREIGN PATENT DOCUMENTS

| | | |
|---|---|---|
| EP | 0 344 773 A2 | 12/1989 |
| EP | 0 420 758 A1 | 4/1991 |

OTHER PUBLICATIONS

A Rajulu et al., *Ultrasonic Studies in Solutions of Polyvinyl Pyrrolidone*, Acustica (1991), vol. 75 No. 3, pp. 213–216.
K. Rao et al., *Acoustical Parameters of Polyvinyl Pyrrolidone Solutions*, Acta Polymerica. (1989), vol. 40 No. 12, pp. 743–746.
S. Kato et al., *Ultrasonic Absorption in Aqueous Polyvinyl Pyrrolidone Solutions*, Nippon Kagaku Kaisha (1974), vol. 10.
JP 02092343, Acoustic Coupler for Ultrasonic Probe and Preparation Thereof (Abstract), Katayama Tetsuya, 1988.

* cited by examiner

Primary Examiner—Marvin M. Lateef
Assistant Examiner—Jeoyuh Lin
(74) Attorney, Agent, or Firm—Welsh & Katz, Ltd.

(57) ABSTRACT

A coupling medium for high-power ultrasound including a liquid aqueous solution of a hydrophilic polymer, notably polyvinylpyrrolidone, is provided together with ultrasound therapy apparatus including a therapy transducer adapted to transmit high-power ultrasound arranged in an enclosure, a portion of which is filled with the coupling medium.

15 Claims, No Drawings

COUPLING MEDIUM FOR HIGH-POWER ULTRASOUND

Applicants claim benefit of priority of French Application No. 99 03 738 filed Mar. 25, 1999, entitled Coupling Medium For High-Power Utrasound.

BACKGROUND OF THE INVENTION

The present invention relates to the field of ultrasound, and more precisely to the field of powerful ultrasound employed for therapeutic purposes, and notably for creating lesions in tissue.

The use of ultrasound for diagnostic purposes in ultrasound scan apparatus is known; such apparatus generally consists of a simple probe which is applied against the patient. In order to improve ultrasound coupling, the use of a coupling gel between the probe and the patient's skin is known. This gel is applied as a thin layer to the patient's skin before examination starts.

Japanese Patent application 2 92343 discloses a coupling product for ultrasound imaging formed by a matrix of porous material such as polyurethane, containing an aqueous gel such as polyvinylpyrrolidone(PVP).

Ultrasound is also used for therapeutic purposes for destroying concretions, mainly by a mechanical effect(shock waves), or in order to create lesions in the tissue, principally by a thermal effect. The apparatus employed in this invention includes a transducer arranged inside a flexible or rigid enclosure, filled with a coupling liquid, which may be water. The enclosure is applied against the patient close to the region to be treated. If needs be, a coupling gel can be employed between the enclosure and the patient's tissue. The distance of propagation inside the coupling liquid is greater than is the case with a coupling gel for ultrasound scanning.

The following can be cited as examples of ultrasound treatment apparatus consisting of endo-cavitary hypothermia apparatus: French Patent applications serial numbers: 91 02620, 93 09158, 96 08096, 94 01304 or 94 06539; such apparatus is adapted to treat the prostate by endo-rectal methods, and includes a focused therapy probe able to produce tissue heating at the focal point, which leads to tissue necrosis at the focal point.

The invention applies notably to the field of therapeutic treatment of tissue by focused ultrasound and more particularly to the field of destruction of tissue inside an organism by causing elevated temperatures using focused ultrasound. In the general area of focused ultrasound, as is known by those skilled in the art, different types of treatment can be distinguished: the earliest treatment to appear was treatment by lithotripsy, which applies to the destruction of hard bodies. This type of treatment employs shock waves, in other words, brief high-power pulses. Later, it was proposed to treat soft tissue by hyperthermia by heating tissue to temperatures not excessively high, in other words, less than 45° C. Hyperthermia involves sending long ultrasound pulses of lower power towards the tissue to be treated. Finally, treatment of the soft tissue using high intensity focused ultrasound, generally known by the acronym HIFU, is being proposed. HIFU treatment consists in heating tissue to elevated temperatures typically greater than 45° C. Focused ultrasound treatment at high intensity represents an effective means for creating lesions by necrosis from coagulation in biological tissue with a view to treating localized tumors.

Beyond a certain power threshold, ultrasound creates cavitation phenomena in the media through which it is propagated. Apart from the mechanical effects of cavitation, the bubbles created by cavitation are an obstacle to ultrasound propagation. The cavitation phenomenon becomes increasingly serious as ultrasound power increases. Such cavitation phenomena are not produced in ultrasound scanning, as the intensity of the ultrasound employed is below the cavitation threshold of the coupling agent. Additionally, in ultrasound scanning applications, the thickness of coupling agent is such that ultrasound absorption by the coupling gel is of secondary importance.

In the case of therapy devices that include additional monitoring by ultrasound scanning, as in the applications mentioned above, the presence of bubbles brought about by cavitation can additionally hinder imaging or may simply be a problem for distance measurement even if the cavitation bubbles do not present a problem for the passage of therapy ultrasound. Notably, when measuring distances by ultrasound in A-mode, the cavitation bubbles create spurious echoes which interfere with and falsify measurement.

U.S. Pat. No. 5,445,813 to Schneider et al. discloses an injectable suspension based on micro-bubbles used as a contrast agent for ultrasound scanning. This suspension acts as a reflector towards ultrasound; it is echogenous.

This use teaches against the aims of the present invention as it tends to increase absorption by ultrasound of low power. In this invention, use of decreasing cavitation brought about by the high-power ultrasound is proposed.

A Rajulu et al., in *Ultrasonic studies in solutions of polyvinylpyrrolidone*, Acustica (1991), volume 75 No. 3, pages 213–6 evaluates the properties of aqueous solutions of PVP for determining variations in adiabatic compressibility as a function of temperature, viscosity, and molar ratio between polyvinylpyrrolidone and the solvent.

K. Rao et al., *Acoustical parameters of polyvinylpyrrolidone solutions*, Acta polym. (1989), vol. 40 No. 12, pages 743–6 demonstrate the presence of a complex with H-shaped bonds for aqueous solutions of PVP at varying concentrations, starting from a study of the speed of propagation of ultrasound, of viscosity and refractive index.

S. Kato et al., *Ultrasonic absorption in aqueous polyvinylpyrrolidone solutions*, Nippon Kagaku Kaisha (1974), Vol. 10, discusses the behavior in absorption of aqueous solutions of PVP between 5 and 130 MHz and between 10 and 40° C.

These documents neither disclose nor suggest the use of aqueous solutions of PVP or another hydrophilic polymer as a coupling medium for high-power ultrasound.

U.S. Pat. No. 5,078,149 discloses an ultrasound coupling device having a recipient containing a polymer gel; the coupling device is designed to be arranged between an ultrasound scan probe and the patient to be investigated. One of the polymer gels proposed in that reference is a 3-dimensionally radiation-hardened PVP solution. That reference, however, only mentions applications for ultrasound scanning, and does not disclose or suggest the problem of cavitation, its solutions, or applications involving treatment by high-power ultrasound.

Additionally, high-power transducers need to be cooled. Accordingly, the coupling medium that is in contact with them should be pumpable (liquid), which excludes viscous media.

There is consequently a need for a liquid coupling medium which is suitable for transmission of ultrasound at the frequencies and the energy levels typically employed for ultrasound therapy treatment, which makes it possible to avoid as much as possible cavitation phenomena. Preferably, such a coupling medium should have an absorption which is as low as possible in the frequency range of the ultrasound employed.

This problem occurs notably in hyperthermia apparatus but is also encountered in other treatment apparatus using high-power ultrasound.

The present invention discloses a solution to this problem.

SUMMARY OF THE INVENTION

More precisely, there is a provided a coupling medium for high-power ultrasound comprising a liquid aqueous solution of a hydrophilic polymer. A preferred hydrophilic polymer is polyvinylpyrrolidone.

The molecular weight of the hydrophilic polymer is preferably between 10,000 and 100,000. In a preferred embodiment, the amount of polymer is between 10 and 50 g/l.

The present invention also provides an ultrasound therapy apparatus, which includes a therapy transducer adapted to transmit high-power ultrasound, arranged in an enclosure filled with the above coupling medium. The apparatus preferably includes an ultrasound generator coupled to the transducer, which transmits ultrasound in a frequency range between 1 and 5 MHz, and preferably between 2 and 3 MHz. In one embodiment, the apparatus further includes an imaging transducer.

The apparatus may further include a device for measuring the distance to the target using ultrasound employing an A-mode ultrasound technique (A-mode echography). In one embodiment, the apparatus further includes means for recirculating the coupling medium.

Further characteristics and advantages of the invention will become more clear from the description which follows, which is provided only by way of example.

DETAILED DESCRIPTION

The coupling medium of the invention is adapted to highpower ultrasound. Here, the expression "high-power ultrasound" should be taken to mean all ultrasound able to create tissue damage or necrosis, in particular, thermal damage or damage induced by cavitation, such damage being the aim of the ultrasound (unlike ultrasound used for scanning which occasionally creates unintentional damage). This high-power ultrasound is also intended to mean therapy ultrasound in the instant application; both terms are equal. The high-power or therapy ultrasound has typically an energy density higher than 1,000 W/cm$^2$.

The coupling medium of the invention is a liquid aqueous solution of a hydrophilic polymer. The solution is liquid, thus it pumpable, and can thus serve as a cooling fluid for the transducer, and/or for the probe, notably in the case of an endorectal probe, and/or for neighboring tissue and/or for the tissue to be treated.

Here, the expression "hydrophilic polymer" means any substance of a high molecular weight, (for example greater than 300) having sufficient affinity for water as to dissolve therein or form a gel with it. Examples of such polymers are: polyvinylpyrrolidone, acrylic polymers, poly(vinyl alcohol), cellulose derivatives (such as alkyl cellulose, hydroxypropyl cellulose, hydroxymethyl cellulose, hydroxypropylmethyl cellulose, carboxymethyl cellulose), gelatine, gums (guar, agaragar, etc), polyethylene oxide, etc. Polymer mixtures are also suitable. Molecular weight may be, for example, between 10,000 and 100,000 and, preferably is between 30,000 and 75,000.

The preferred hydrophilic polymer is polyvinylpyrrolidone (PVP). The PVP employed in the framework of this invention is for example PLASDONE, notably K 29–32 (with a molecular weight about 58,000).

Polymer concentration in the aqueous medium can vary over a wide range, as determined by the person skilled in the art. Generally, the amount of polymer is between 10 and 50 g/l. When used in this amount, the hydrophilic polymer does not lead to a gelified solution, unlike in the prior art. The viscosity of the solution of the invention is substantially that of water (which is 1 cst (centistoke) at 20° C). The viscosity of the solution according to the present invention is between 1 and 2 cst, preferably between 1.2 and 1.6 cst, at 20° C. For example, this viscosity is 1.3 cst for a 10 g/l. concentration PVP solution.

The solution according to the invention has substantially the same acoustic and absorption characteristics as those of water. The solution according to the invention has identical attenuation to that of water, for example, for PVP solutions at a concentration of 10 and 20 g/l.

The low acoustic absorption, or the low acoustic attenuation of the coupling medium of the invention ensures that a major portion of the high-power ultrasound is effectively transmitted towards the region to be treated.

In terms of cavitation, the invention also provides a substantial improvement compared to the known use of water as the coupling medium. The coupling medium of the invention consequently makes it possible to reduce cavitation effects without leading to an increase in ultrasound absorption. It provides excellent therapy ultrasound transmission and additionally, it ensures that the imaging device, if present, supplies a sharp image of the region to be treated, and that the measuring device, notably using A-mode ultrasound measurement, provides the correct distance to the target.

The coupling medium of the invention is a water-based medium; it is consequently easy to prepare and use, and does not require particular precautions to be taken during use. It has the advantage of being relatively fluid and, where the transducer is contained inside a flexible casing, consequently readily adapts to the morphology of the treated region.

The coupling medium of the invention may contain conventional additives, such as stabilizers, anti-bacterial agents (for example amphorisine) and others. The coupling medium of the invention additionally has an acoustic impedance which is close to that of water.

The speed of propagation in the medium of the invention is also substantially equal to that in water. By way of example, propagation speeds in the solution of the invention are identical for PVP solutions at concentrations of from 10 to 20 g/l., to those in water augmented respectively by 3% and 5%.

Identity of propagation speeds and impedance permits the coupling medium of the invention to be used in existing therapy apparatus with no need to modify them. Additionally, the use of a coupling medium having such propagation characteristics avoids loss of focus, and reflections at interfaces. A coupling medium is obtained which substantially has the propagation characteristics of human body tissue, thereby ensuring good focusing and good transmission, notably at interfaces.

The invention additionally may include an ultrasound treatment apparatus comprising a therapy transducer arranged inside an enclosure containing such a coupling medium. This enclosure can be rigid, flexible or partially flexible. The apparatus may include an ultrasound generator suitable for generating therapy ultrasound, for example, ultrasound in the frequency range of a generator transmitting ultrasound in the frequency range of from 1 to 5 MHz, preferably from 2 to 3 MHz.

Preferably, the apparatus of the invention also includes an imaging transducer, which also supplies an image of the treated region. Preferably, the apparatus of the invention includes an A-mode ultrasound measuring device working from the therapy transducer, the device being a transmission-reception element TV incorporated into the transducer (sending of a pulse and measuring the time for the pulse to return, i.e. measurement of the echo time). Using a coupling medium according the invention makes it possible to ensure that such a device also supplies a sharp image and/or measurement of the distance to the target that is reliable.

The following example illustrates the invention without limiting it.

EXAMPLE

PLASDONE K29-32 solutions at concentrations of 10, 20 and 50 g/l were prepared. Fluid solutions of liquid consistency were obtained. The coupling medium of the invention had absorption characteristics that are very close to those of water.

The coupling medium was introduced into a therapy apparatus of the type sold by applicant under the name "ABLATHERM". Apart from having no influence at therapeutic effect levels, this coupling medium prevented spurious echoes during measurement of the distance to the target using A-mode ultrasound measurement.

Obviously, this invention is not limited to the examples and embodiments described and illustrated but may be subject to numerous variations readily accessible to those skilled in the art.

What is claimed is:

1. An ultrasound therapy apparatus comprising:
   a therapy transducer adapted to transmit high-power ultrasound, the therapy transducer housed in an enclosure filled with a coupling medium, the coupling medium comprising a liquid aqueous solution of a hydrophilic polymer having a molecular weight of between 30,000 and 75,000; and
   means for recirculating the coupling medium.

2. The apparatus according to claim 1, wherein the coupling medium is polyvinylpyrrolidone.

3. The apparatus according to claim 1 wherein the amount of polymer is about between 10 g/l. and 50 g/l.

4. The apparatus according to claim 1 further comprising an ultrasound generator coupled to the transducer, the generator configured to cause the transducer to transmit ultrasound in a frequency range between 1 and 5 MHz.

5. The apparatus according to claim 1 further comprising an imaging transducer.

6. The apparatus according to claim 1 further comprising a device for measuring a distance to a target using A-mode ultrasound.

7. The apparatus according to claim 1 wherein the therapy transducer is surrounded by flexible or partially flexible enclosure, a portion of the enclosure filled with the hydrophilic polymer.

8. The apparatus according to claim 1 wherein the therapy transducer is surrounded by a rigid or partially rigid enclosure, a portion of the enclosure filled with the hydrophilic polymer.

9. An ultrasound therapy apparatus comprising:
   a therapy transducer adapted to transmit high-power ultrasound;
   the therapy transducer housed in an enclosure, a portion of the enclosure filled with a coupling medium, the coupling medium comprising a liquid aqueous solution of a hydrophilic polymer having a molecular weight of between 30,000 and 75,000;
   an ultrasound generator coupled to the transducer, the generator configured to cause the transducer to emit ultrasound in a frequency range between 1 and 5 MHz; and
   means for recirculating the coupling medium.

10. The apparatus according to claim 9, wherein the coupling medium is polyvinylpyrrolidone.

11. The apparatus according to claim 9 wherein the amount of polymer is about between 10 g/l. and 50 g/l.

12. The apparatus according to claim 9 further comprising an imaging transducer.

13. The apparatus according to claim 9 further comprising a device for measuring a distance to a target using A-mode ultrasound.

14. The method according to claim 13, wherein the ultrasound transducer is surrounded by flexible or partially flexible enclosure, a portion of the enclosure filled with the hydrophilic polymer.

15. The method according to claim 13, wherein the ultrasound transducer is surrounded by a rigid or partially rigid enclosure, a portion of the enclosure filled with the hydrophilic polymer.

* * * * *